ated under 35
United States Patent
Shepherdson et al.

(10) Patent No.: US 10,506,811 B1
(45) Date of Patent: Dec. 17, 2019

(54) ANTI-MICROBIAL SOLUTION FOR SEEDS, CROPS, LIVESTOCK AND PROCESSED FOODS

(71) Applicant: Pur Products LLC, Berwyn, PA (US)

(72) Inventors: Lance Shepherdson, Warwickshire (GB); Harold D. Grant, Berwyn, PA (US)

(73) Assignee: Pur Products LLC, Berwyn, PA (US)

( * ) Notice: Subject to any disclaimer, the term of this patent is extended or adjusted under 35 U.S.C. 154(b) by 0 days.

(21) Appl. No.: 16/198,132

(22) Filed: Nov. 21, 2018

(51) Int. Cl.
*A01N 59/08* (2006.01)
*A01N 25/02* (2006.01)
*C01B 11/06* (2006.01)

(52) U.S. Cl.
CPC .............. *A01N 59/08* (2013.01); *A01N 25/02* (2013.01); *C01B 11/06* (2013.01)

(58) Field of Classification Search
None
See application file for complete search history.

(56) References Cited

U.S. PATENT DOCUMENTS

| | | | |
|---|---|---|---|
| 6,180,566 B1 | 1/2001 | Nielsen et al. | |
| 6,221,944 B1 | 4/2001 | Liebeskind et al. | |
| 6,927,237 B2 | 8/2005 | Hei et al. | |
| 6,962,714 B2 | 11/2005 | Hei et al. | |
| 6,964,787 B2 * | 11/2005 | Swart | A23B 4/015 |
| | | | 422/22 |
| 7,588,488 B2 * | 9/2009 | Hopkins | A22C 21/0061 |
| | | | 452/123 |
| 9,743,668 B2 | 8/2017 | Ramsay et al. | |
| 9,872,490 B2 | 1/2018 | Lindner | |
| 2003/0139310 A1 | 7/2003 | Smith et al. | |
| 2005/0252538 A1 | 11/2005 | Vernon et al. | |
| 2007/0023273 A1 | 2/2007 | Kitaori et al. | |
| 2007/0042094 A1 | 2/2007 | Wart et al. | |
| 2009/0148342 A1 | 6/2009 | Bromberg et al. | |
| 2010/0009889 A1 | 1/2010 | Smith et al. | |
| 2016/0073599 A1 | 3/2016 | Wargent | |
| 2017/0258093 A1 | 9/2017 | Meccia et al. | |
| 2017/0303554 A1 | 10/2017 | Mathieu et al. | |

FOREIGN PATENT DOCUMENTS

JP 2000109887 4/2000
WO WO 2003073849 9/2003

OTHER PUBLICATIONS

Koseki, S. et al., "Efficacy of acidic electrolyzed water for microbial decontamination of cucumbers and strawberries" J. Food Prot. Jun. 2004, pp. 1247-1251.

* cited by examiner

*Primary Examiner* — Celeste A Roney
(74) *Attorney, Agent, or Firm* — Joseph E. Maenner; Maenner & Associates, LLC

(57) ABSTRACT

An anti-microbial formulation for seed and crop application includes about 170 ppm hypochlorous acid; about 25 ppm hypochlorite ion; about 2.5 ppm ozone; about 2.5 ppm chlorine dioxide; between about 10 ppm and about 100,000 ppm alkyl polyglycoside; and a remainder of water. A method of manipulating the pH of the formulation and a method of treating seeds and crops with the formulation to restrict or eliminate microbial growth and proliferation is also described herein.

15 Claims, 4 Drawing Sheets

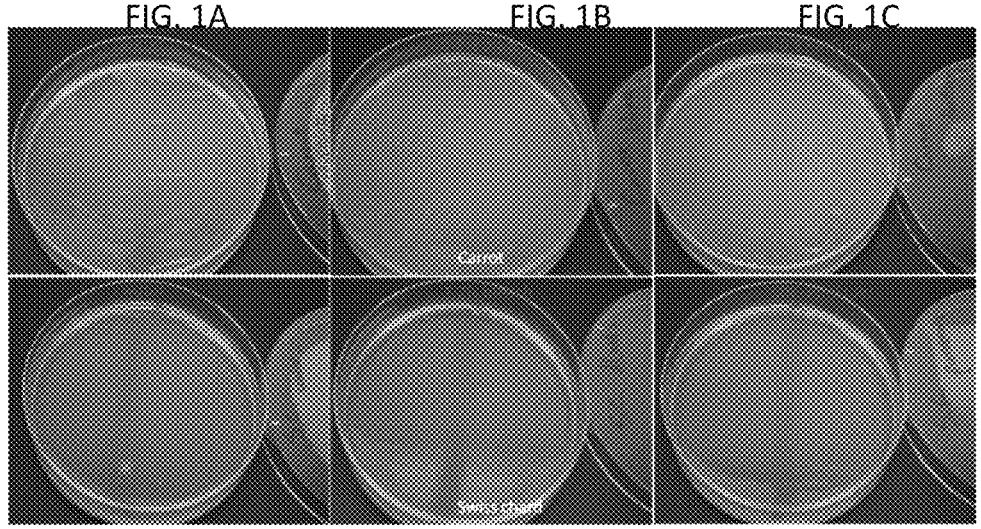
FIG. 1A  FIG. 1B  FIG. 1C
FIG. 1D  FIG. 1E  FIG. 1F
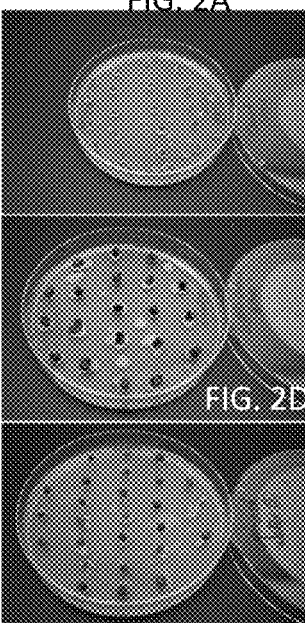
FIG. 2A  FIG. 2B  FIG. 2C
FIG. 2D  FIG. 2E  FIG. 2F
FIG. 2G  FIG. 2H  FIG. 2I

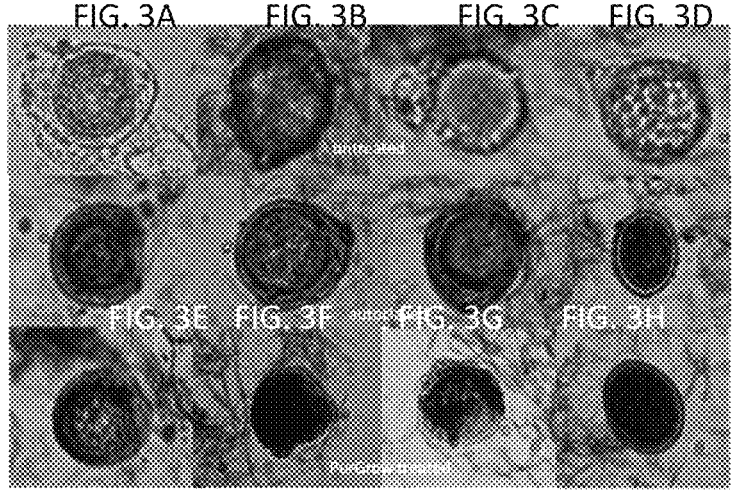
FIG. 3A  FIG. 3B  FIG. 3C  FIG. 3D
FIG. 3E  FIG. 3F  FIG. 3G  FIG. 3H
FIG. 3I  FIG. 3J  FIG. 3K  FIG. 3L
FIG. 4A  FIG. 4B
FIG. 4C  FIG. 4D

US 10,506,811 B1

ANTI-MICROBIAL SOLUTION FOR SEEDS, CROPS, LIVESTOCK AND PROCESSED FOODS

BACKGROUND OF THE INVENTION

Field of the Invention

The present invention relates to an anti-microbial solution for application to seeds, crops, livestock and processed foods.

Description of the Related Art

Crop production can be negatively impacted by plant diseases. During the growing season and throughout a plant's growth cycle, plants may be attacked by a number of microorganisms, including fungi, fungal-like organisms, bacteria, viruses etc. These diseases can cause significant damage to plants, reducing both the yield and quality of the agricultural commodities.

Plant pathogens are common on seed of virtually all crops. These seedborne pathogens may be internal, infecting plants through flower or fruits, or on the seed surface. External contamination on the surface of seed is common whereby plant pathogens produce a wide range of survival structures (for example spores, oospores, chlamydospores etc.) that stick to the surface of seed or plant during its growth, harvesting, processing and packaging. The infestation or infection of a seed reduces the quantity and quality of the gemination rate of the seed, thus decreasing the number of seedlings that survive. Infected or diseased seeds transfer the pathogens that they carry not only to the soil but to the other plants that are in their proximity, thereby initiating epidemics.

Seeds can be cleaned of plant pathogens by several physical and/or chemical approaches. Hot water treatment can be an effective method to reduce or eliminate some seedborne plant pathogens. However, the temperature and duration of the hot water treatments varies for different crops and it is difficult to standardize the approach so that the seed itself is not damaged. The efficacy and impact on seed germination rates of hot water treatment are questionable. Some fungicide treatments may be effective for certain pathogens but not others. However, the cost of fungicide, labor, and environmental impacts are a major concern. Moreover, synthetic fungicides cannot be used on any organic crop production. Sodium hypochlorite (bleach) may be effective for controlling a wide-spectrum of plant pathogens. However, only a low percentage of bleach (1.2%) may be used use on seed being grown for organic production. But the efficacy and phytotoxicity of even low concentrations of bleach limit the potential use.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a formulation that can be used to treat crops from the seed stage through the growth cycle to consumption. The formulation kills or impedes the growth of microbes, including pathogens, germs, viruses, molds, mildews, fungi, and spores on contact on the surface of the seeds.

In another embodiment, the present invention is a method of manipulating the pH of the formulation.

In still another embodiment, the present invention is a method of treating seeds and crops to restrict or eliminate microbial growth and proliferation.

BRIEF DESCRIPTION OF THE FIGURES

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1A is a photo showing a significant growth of bacteria on carrot seeds present in water;

FIG. 1B is a photo showing some bacteria on carrot seeds in 1.2% bleach;

FIG. 1C is a photo showing no bacteria on carrot seeds in the 50% formulation;

FIG. 1D is a phorot showing a significant growth of bacteria on Swiss chard seeds in water (FIG. 1D);

FIG. 1E is a photo showing some bacteria Swiss chard seeds in 1.2% bleach;

FIG. 1F is a photo showing no bacteria on Swiss chard seeds in the 50% formulation;

FIG. 2A is a photo showing three days after the carrot seeds from FIG. 1A placed on LB plates, bacteria were found from each carrot seed washed with water;

FIG. 2B is a photo showing bacteria found on about 50% of the carrot seed from FIG. 1B washed with 1.2% bleach;

FIG. 2C is a photo showing bacteria found on only a few carrot seeds from FIG. 1C washed with the formulation;

FIG. 2D is a photo showing bacteria found from all Swiss chard seed from FIG. 1D washed with water;

FIG. 2E is a photo showing bacteria found on about 50% Swiss chard seed from FIG. 1E treated with 1.2% bleach;

FIG. 2F is a photo show in bacteria found on only a few seeds treated with the formulation;

FIG. 2G is a photo showing spinach seed washed with water, with bacteria found from almost every single seed;

FIG. 2H is a photo showing both fungal and bacterial microbes found on spinach seeds treated with 1.2% bleach;

FIG. 2I is a photo showing bacteria found from several seeds treated with the formulation;

FIG. 3A is a photo showing untreated oospores that cannot be stained by Trypan blue);

FIG. 3B is a photo showing other untreated oospores that cannot be stained by Trypan blue);

FIG. 3C is a photo showing other untreated oospores that cannot be stained by Trypan blue);

FIG. 3D is a photo showing other untreated oospores that cannot be stained by Trypan blue);

FIG. 3E is a photo showing dead oospores (killed by autoclave) that can be stained;

FIG. 3F is a photo showing other dead oospores (killed by autoclave) that can be stained;

FIG. 3G is a photo showing other dead oospores (killed by autoclave) that can be stained;

FIG. 3H is a photo showing other dead oospores (killed by autoclave) that can be stained;

FIG. 3I is a photo showing oospores treated with the formulation that were also stained, indicating that these oospores were also killed by the formulation;

FIG. 3J is a photo showing other oospores treated with the formulation that were also stained, indicating that these oospores were also killed by the formulation;

FIG. 3K is a photo showing other oospores treated with the formulation that were also stained, indicating that these oospores were also killed by the formulation;

FIG. 3L is a photo showing other oospores treated with the formulation that were also stained, indicating that these oospores were also killed by the formulation;

FIG. 4A is a photo showing rice cultivar Francis sprayed daily with the formulation since the inoculation day (0 dpi);

FIG. 4B is a photo showing rice cultivar Francis sprayed with the formulation daily since 1 dpi;

FIG. 4C is a photo showing rice cultivar Francis sprayed with the formulation daily since 2 dpi;

FIG. 4D is a photo showing rice cultivar Francis sprayed with the formulation daily since 3 dpi;

DETAILED DESCRIPTION

Figure 4E:
FIG. 4E is a photo showing rice plants where the inoculation plugs of *Rhizoctonia solani* were placed, with not much pathogen found growing and infecting the plants that were sprayed since the first day of inoculation.

Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

A formulation in the form of a liquid fungicidal sporicidal antimicrobial solution according to an exemplary embodiment of the present invention can be used as a surface sanitizer, a wash, or a treatment for crop seeds to kill or reduce the growth of microbes, including pathogens, germs, viruses, molds, mildews, fungi, and spores on contact on the surface of the seeds. The crops can be vegetables, fruits, herbs, or other naturally growing organism that is harvested for human or animal use or consumption.

The formulation is a safe product which has no known adverse effect on humans or environment. Thus, the formulation can be widely used as a seed treatment on seed for agricultural production, including seed for organic production. The formulation can kill a wide range of microbial plant pathogens. Experimental results indicated that the formulation can be used to surface-sterilize seed, killing spores and oospores of the plant pathogens on the external surface of seed. Spraying the formulation on plants can dramatically reduce the level of pathogens and infection in the field and thus, control or minimize disease. The formulation can be added to irrigation water, and thus may reduce the populations of soilborne pathogens. Washing agricultural products such as vegetables, fruits, livestock and processed foods with the formulation can reduce the level of common bacteria such as *E. coli* or *Salmonella*, commonly associated with food safety concerns.

The formulation kills or reduces the toxicity of pathogens. Additionally, the solution can be used to kill bacteria on a non-organic surface, in the air, and in water. The formulation halts a microbe's ability to replicate by attacking and de-naturing microbial DNA.

Additionally, the formulation can be applied as a spot treatment on crops and/or applied to the soil in which the seeds are planted. Further, the formulation can be applied to the interior surfaces of pipes and other fluid systems that are used to irrigate or otherwise deliver water or other fluids to crops.

In an exemplary embodiment, for seed treatment with the formulation, the formulation can be added at a rate of ⅓ liter of the formulation for every ton of seeds. This ratio can vary, however, due to the type of seed cleaning system that is used, along with local temperature, which can have an effect on drying times. Further, the formulation can be applied in an irrigation system ad a ratio of about 0.5% to about 1.5% by weight of the irrigation fluid. The formulation can also be used during the washing/cleaning of cut crops, typically dosed in baths, at a rate of between about 1% and about 3% by weight of the cleaning fluid, depending on the quality of the fluid, such as hard/soft water, amount of particulates in the water, and other factors.

In an exemplary embodiment, the formulation is a solution having a pH of about 7.0 and has the following formula:
Hypochlorous acid—about 170 parts per million ("ppm")
Hypochlorite ion—about 25 ppm
Ozone—about 2.5 ppm
Chlorine dioxide—about 2.5 ppm
Alkyl polyglycoside—about 300 ppm
Water—remainder The alkyl polyglycoside acts to break down the molecular structure of the solution so that the solution attaches to, rather than merely lays on, a crop leaf, seed, or other surface on which the solution is applied. As a result, larger crop coverage is provided with less solution than if alkyl polyglycoside was not used.

Optionally, in one embodiment, the water can be electrolyzed water. The electrolyzed water (EO) is generated by passing an electrical current through a dilute salt water solution. One byproduct of the reaction is sodium hydroxide (NaOH) and another by product is hypochlorous acid, which as a low pH, contains active chlorine, and has a strong oxidation-reduction potential similar to ozone. The inventors have discovered that using EO water resulted in surface microbial counts 1 log lower than when an iodophor sanitizer was used.

In order for the formulation to be classified as an "organic" solution, it is desired that there be less than 1.2% by weight bleach in the formulation. In an exemplary embodiment, the formulation has no (0%) bleach. Ozone is used instead of bleach because ozone has more cleaning power than bleach. Ozone can act up to 2,000 faster than bleach and is more effective than bleach.

The formulation can be applied throughout any temperature range between freezing and boiling, although an exemplary temperature range matching a particular crop or livestock's growth needs can be used The solution can be separated into an acidic portion (containing the hypochlorous acid) and an alkaline portion (containing the alkyl polyglycoside). The solution can be passed through a cell or membrane that separates the acidic portion from the alkaline portion and stores the acidic portion in the first location and stores the alkaline portion in a second location.

To form a final formulation having a desired pH, at least some of the alkaline portion is recombined with the acidic portion at a desired titration level to produce a desired pH. The desired pH is determined prior to recombining the alkaline portion with the acidic portion so that a predetermined amount of the alkaline portion is recombined with the acidic portion. The alkyl polyglycoside in the recombined solution can be varied between about 10 and about 100,000 ppm such that, when the amount of alkyl polyglycoside is closer to 10 ppm, then the solution becomes acidic. When the amount of alkyl polyglycoside is closer to 100,000 ppm, then the solution becomes alkaline.

In an exemplary embodiment, the solution has a pH of between about 6.0 and about 7.0. Those skilled in the art, however, will recognize that the pH of the solution can be adjusted such as, for example, by altering the amount of alkyl polyglycoside so that the pH can be adjusted between about 2.0 and about 12.0. For example, if an acidic solution is required to suit particular seeds and/or soil conditions, the pH can be reduced toward 2.0.

By way of example, the following crops are acid soil crops and prefer a pH of 4 to 5.5:
Blackberry (5.0-6.0)
Blueberry (4.5-5.0)
Cranberry (4.0-5.5)
Parsley (5.0-7.0)
Peanut (5.0-7.5)
Potato (4.5-6.0)
Raspberry (5.5-6.5)
Sweet potato (5.5-6.0)

By way of example, the following crops are somewhat acid soil crops and prefer a somewhat acid soil, having a pH of 5.5 to 6.5:
Apple (5.0-6.5)
Basil (5.5-6.5)
Carrot (5.5-7.0)
Cauliflower (5.5-7.5)
Chervil (6.0-6.7)
Corn (5.5-7.5.)
Cucumber (5.5-7.0)
Dill (5.5-6.5)
Eggplant (5.5-6.5)
Garlic (5.5-7.5)
Melon (5.5-6.5)
Parsley (5.0-7.0)
Pepper (5.5-7.0)
Pumpkin (6.0-6.5)
Radicchio (6.0-6.7)
Radish (6.0-7.0)
Rhubarb (5.5-7.0)
Sorrel (5.5-6.0)
Squash, winter (5.5-7.0)
Sweet potato (5.5-6.0)
Tomato (5.5-7.5)
Turnip (5.5-7.0)

By way of example, the following crops are moderately alkaline soil plants and will tolerate a pH of 6.0 to 7.0 or greater:
Artichoke (6.5-7.5)
Arugula (6.5-7.5)
Asparagus (6.0-8.0)
Bean, pole (6.0-7.5)
Bean, lima (6.0-7.0)
Beet (6.0-7.5)
Broccoli (6.0-7.0)
Broccoli rabe (6.5-7.5)
Brussels sprouts (6.0-7.5)
Cabbage (6.0-7.5)
Cantaloupe (6.0-7.5)
Cauliflower (6.0-7.5)
Celery (6.0-7.0)
Chinese cabbage (6.0-7.5)
Celeriac (6.0-7.0)
Celery (6.0-7.0)
Chinese cabbage (6.0-7.5)
Chive (6.0-7.0)
Cilantro (6.0-6.7)
Claytonia (6.5-7.0)
Collard (6.5-7.5)
Cress (6.0-7.0)
Endive/escarole (6.0-7.0)
Fennel (6.0-6.7)
Gourd (6.5-7.5)

Horseradish (6.0-7.0)
Jerusalem Artichoke/Sunchoke (6.7-7.0)
Kale (6.0-7.5)
Kohlrabi (6.0-7.5)
Leek (6.0-8.0)
Lettuce (6.0-7.0)
Marjoram (6.0-8.0)
Mizuna (6.5-7.0)
Mustard (6.0-7.5)
Okra (6.0-7.5)
Onion (6.0-7.0)
Oregano (6.0-7.0)
Pak choi (6.5-7.0)
Parsnip (5.5-7.5)
Pea (6.0-7.5)
Radicchio (6.0-6.7)
Radish (6.0-7.0)
Rhubarb (6.5-7.0)
Sage (6.0-6.7)
Salsify (6.0-7.5)
Spinach (6.0-7.5)
Squash, summer (6.0-7.0)
Sunflower (6.0-7.5)
Sunflower (6.0-7.5)
Swiss chard (6.0-7.5)
Tarragon (6.0-7.5)
Tomatillo (6.7-7.3)
Watermelon (6.0-7.0)

By way of example, the following crops are very acid to alkaline soil tolerant plants. These crops have the greatest tolerance for a wide range of soil acidity or alkalinity, from about 5.0 to 7.0:

Alpine strawberry (5.0-7.5)
Carrot (5.5-7.0)
Cauliflower (5.5-7.5)
Corn (5.5-7.5)
Cucumber (5.5-7.0)
Dill (5.5-6.7)
Endive/Escarole (5.8-7.0)
Garlic (5.5-7.5)
Parsley (5.0-7.0)
Parsnip (5.5-7.5)
Peanut (5.0-6.5)
Pepper (5.5-7.0)
Rutabaga (5.5-7.0)
Squash, winter (5.5-7.0)
Tomato (5.5-7.5)
Turnip (5.5-7.0)

Figure 4F:
FIG. 4F is a photo showing severe disease found from the plants that were sprayed only on 6 dpi.
Figure 5A:
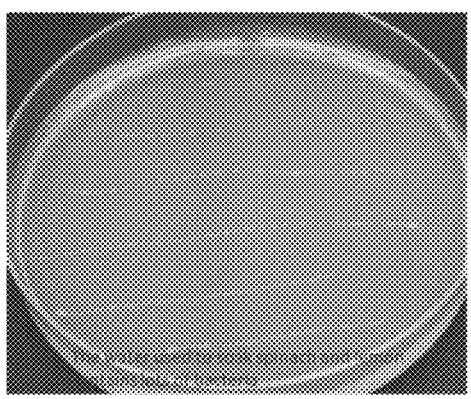
FIG. 5A is a photo showing significant amount of bacteria found from the water used to soak spinach leaves and lemons.
Figure 5B:
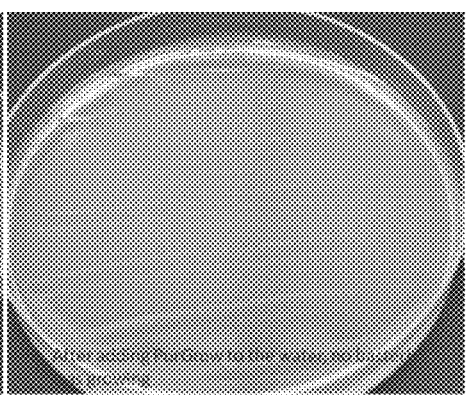
FIG. 5B is a photo showing no bacteria found alive from the water added formulation.
Figure 5C:
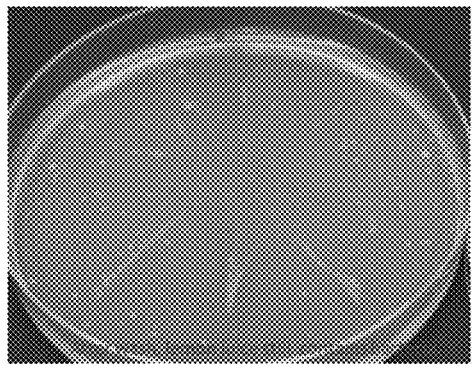
FIG. 5C is a photo showing bacteria from the juice squeezed out of contaminated lemon slides.
Figure 5D:
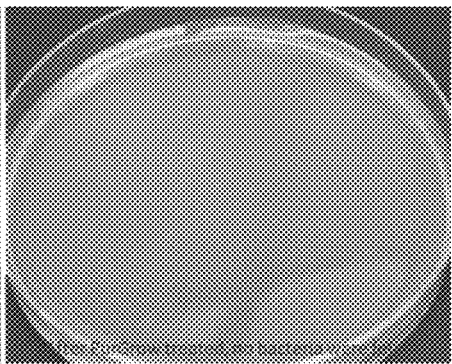
FIG. 5D is a photo showing no bacteria found alive from the juice squeezed out of the lemon slides treated with the formulation.
Figure 5E:
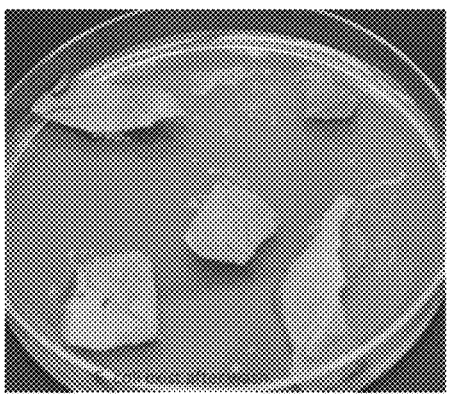
FIG. 5E is a photo showing bacteria found from artificially contaminated spinach leaves, even after washed with tap water.
Figure 5F:
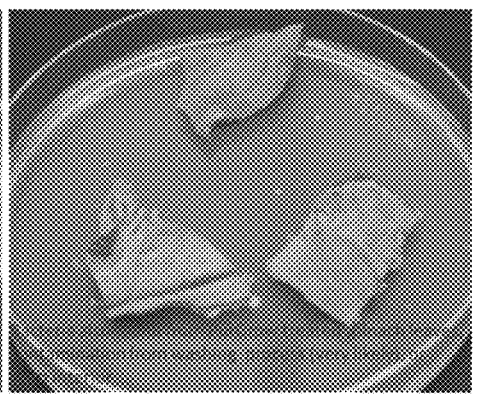
FIG. 5F is a photo showing bacteria found from the spinach leaves treated with the formulation.

The formulation can also be used on other edible and non-edible crops, such as livestock, processed foods, tobacco, and marijuana. The formulation can be used to wash various crops at the end of their growth cycle including before and during packaging, thereby eliminating bacteria and pathogens such as *E. coli, Salmonella* and other dangerous contaminants associated with food safety and consumption.

Experiment 1—Cleaning Vegetable Seed

Carrot, Swiss chard, and spinach seeds (1 kg, 5 kg, and 5 kg respectively) were placed into separate Petri dishes. From each of these seeds, 9 samples were taken, each sample weighing 50 grams. Deionized water, 1.2% bleach, and 50% of the formulation were used to treat three samples of each vegetable for five minutes. The liquid of carrot and Swiss chard treatments were streaked on LB media plates, and kept in a 37 degrees Celsius incubator overnight, and inspected for bacterial growth on the following day. The treated seed were dried in 40 C oven for three days, and some seeds were placed on LB or PDA plates.

After carrot seeds were washed, a significant growth of bacteria was present in water (FIG. 1A), some bacteria in 1.2% bleach (FIG. 1B), but no bacteria in the 50% formulation (FIG. 1C). After Swiss chard seeds were washed, there were also a significant growth of bacteria in water (FIG. 1D), some bacteria in the 1.2% bleach (FIG. 1E), but no bacteria in the 50% formulation (FIG. 1F).

Three days after the carrot seeds placed on LB plates, bacteria were found from each carrot seed washed with water (FIG. 2A), about 50% of the carrot seed washed with 1.2% bleach (FIG. 2B), and only a few carrot seed washed with the formulation (FIG. 2C). Fugal mycelium was growing out from some carrot seeds. These carrot seeds may be interiorly infected by a fungal pathogen too.

Similar results were also obtained for Swiss chard washing experiment. Bacteria were found from all Swiss chard seed washed with water (FIG. 2D), about 50% Swiss chard seed treated with 1.2% bleach (FIG. 2E), and a few seeds treated with the formulation (FIG. 2F).

From the spinach seed washed with water, mainly bacteria were found from almost every single seed (FIG. 2G). However, both fungal and bacterial microbes were found from the seed treated with 1.2% bleach (FIG. 2H). Bacteria were also found from several seeds treated with the formulation (FIG. 2I). Interestingly, the germination rate of the formulation treatment was higher than that of the bleach and water treatment.

Experiment 2—Treating Oospores of *Peronospora effusa* with the Formulation

Oospores were collected from spinach plants, some of them were autoclaved, some were treated with the formulation overnight, and then all were stained with Trypan blue for 5 minutes. The untreated oospores cannot be stained by Trypan blue (FIGS. 3A-3D), but the dead oospores (killed by autoclave) can be stained (FIGS. 3E-3H). Oospores treated with the formulation were also stained, indicating that these oospores were also killed by the formulation (FIGS. 3I-3L).

Experiment 3—Using the Formulation to Control Rice Blast and Sheath Blight Diseases Rice cultivar Francis was planted in 36 small pots. Three-week old plants were inoculated with *Magnaporthe oryzae* isolate 49D, or *Rhizoctonia solani* isolate VC11 (18 pots for each disease). For each disease inoculation, two pots were sprayed daily with the formulation since the inoculation day (0 dpi) (FIG. 4A), two pots were sprayed with the formulation daily since 1 dpi (FIG. 4B), two pots were sprayed with the formulation daily since 2 dpi (FIG. 4C), two pots were sprayed with the formulation daily since 3 dpi (FIG. 4D), and so on till the 2 pots were sprayed on 6 dpi. On the 7 dpi, disease reactions of rice plants to the two diseases were scored separately.

The rice plants sprayed with the formulation daily since the day of inoculation did not have any lesion of rice blast. The rice plants sprayed with the formulation daily since 1 dpi had some tiny lesions, but these lesions stopped expansion. Typical blast lesions were found on plants sprayed daily with the formulation after 2 dpi.

After spraying the formulation daily to the base of rice plants where the inoculation plugs of *Rhizoctonia solani* were placed, not much pathogen was found growing and infecting the plants that were sprayed since the first day of inoculation (FIG. 4E). Severe disease was found from the plants that were sprayed only on 6 dpi (FIG. 4F). Disease were also found from other plants with different spraying regime.

Experiment 4—Formulation Food Safety Test

Procedures

Grow *E. coli* strain JM109 in LB broth media at 37 C overnight.

At 10 ml culture to 990 ml dH2O for each of two containers. Spinach and lemon slices were soaked in each of the two containers for 24 h.

Add 100 ml of the formulation to one of the containers for 30 min.

Wash spinach and lemon slides with tap water.

Streak the soak water, squeeze lemon juice, or plate spinach leaves on LB agar plate. Incubate the plates at 37 C overnight.

Results

A significant amount of bacteria were found from the water used to soak spinach leaves and lemons (as expected) (FIG. 5A). But no bacteria were found alive from the water added formulation (FIG. 5B).

Bacteria cannot be washed off lemon slides. Many bacteria were from the juice squeezed out of the contaminated lemon slides (FIG. 5C). But no bacteria were found alive from the juice squeezed out of the lemon slides treated with the formulation (FIG. 5D).

Bacteria were found from the artificially contaminated spinach leaves, even after washed with tap water (FIG. 5E). Bacteria were also found from the spinach leaves treated with the formulation. The formulation treated leaves were washed and placed on the LB plates right after the contaminated sample were processed (FIG. 5F). It is possible that there was cross contamination. But it may be resulted from interior contamination although it is very unlikely.

It will be further understood that various changes in the details, materials, and arrangements of the parts which have been described and illustrated in order to explain the nature of this invention may be made by those skilled in the art without departing from the scope of the invention as expressed in the following claims.

We claim:

1. An anti-microbial formulation for seed and crop application comprising:
- about 170 ppm hypochlorous acid;
- about 25 ppm hypochlorite ion;
- about 2.5 ppm ozone;
- about 2.5 ppm chlorine dioxide;
- between about 10 ppm and about 100,000 ppm alkyl polyglycoside; and
- a remainder of water, wherein the formulation is separable from a combined state into an alkaline portion and an acidic portion and subsequently recombinable into the combined state.

2. The anti-microbial formulation according to claim 1, wherein the alkyl polyglycoside is about 300 ppm.

3. The anti-microbial formulation according to claim 2, wherein the formulation has a pH of about 7.

4. The anti-microbial formulation according to claim 1, comprising less than 1.2% by weight of bleach.

5. The anti-microbial formulation according to claim 4, comprising 0% by weight of bleach.

6. The anti-microbial formulation according to claim 1, wherein the water comprises electrolyzed water.

7. The anti-microbial formulation according to claim 1, wherein at least a portion of the alkaline portion is recombinable with the acidic portion.

8. The anti-microbial formulation according to claim 1, wherein the formulation has a pH between about 2 and about 12.

9. The anti-microbial formulation according to claim 8, wherein the formulation has a pH between about 4 and about 9.

10. The anti-microbial formulation according to claim 9, wherein the formulation has a pH between about 6 and about 7.

11. The anti-microbial formulation according to claim 1, wherein the formulation is applicable to seeds and crops.

12. The anti-microbial formulation according to claim 1, wherein the formulation kills or reduces the growth of pathogens, germs, viruses, molds, mildews, fungi, and spores on contact on the surface of seeds.

13. The anti-microbial formulation according to claim 1, wherein the formulation halts a microbe's ability to replicate by attacking and de-naturing microbial DNA.

14. A system consisting of:

a formulation comprising:
- about 170 ppm hypochlorous acid;
- about 25 ppm hypochlorite ion;
- about 2.5 ppm ozone;
- about 2.5 ppm chlorine dioxide;
- between about 10 ppm and about 100,000 ppm alkyl polyglycoside; and
- a remainder of water.

15. A system consisting of:

a formulation comprising:
- about 170 parts hypochlorous acid;
- about 25 parts hypochlorite ion;
- about 2.5 parts ozone;
- about 2.5 parts chlorine dioxide;
- between about 10 parts and about 100,000 parts alkyl polyglycoside; and
- a remainder of water.

* * * * *